United States Patent
Cherukupally et al.

(10) Patent No.: US 9,416,152 B2
(45) Date of Patent: Aug. 16, 2016

(54) AZACITIDINE PROCESS AND POLYMORPHS

(71) Applicants: DR. REDDY'S LABORATORIES LTD., Hyderabad (IN); DR. REDDY'S LABORATORIES, INC., Bridgewater, NJ (US)

(72) Inventors: Praveen Cherukupally, Hyderabad (IN); Satish Kumar Vujjini, Hyderabad (IN); Ganesh Varanasi, Hyderabad (IN); Sreenadha Charyulu Kandala, Hyderabad (IN); Srinivas Areveli, Karimnagar (IN); Satyanarayana Raju Tirumalaraju, Hyderabad (IN)

(73) Assignees: DR. REDDY'S LABORATORIES LTD., Hyderabad (IN); DR. REDDY'S LABORATORIES, INC., Bridgewater, NJ (US)

( * ) Notice: Subject to any disclaimer, the term of this patent is extended or adjusted under 35 U.S.C. 154(b) by 0 days.

(21) Appl. No.: 14/174,143

(22) Filed: Feb. 6, 2014

(65) Prior Publication Data

US 2014/0155588 A1  Jun. 5, 2014

Related U.S. Application Data

(63) Continuation of application No. 13/016,335, filed on Jan. 28, 2011, now Pat. No. 8,703,932, which is a continuation of application No. PCT/US2009/052376, filed on Jul. 31, 2009.

(60) Provisional application No. 61/102,064, filed on Oct. 2, 2008, provisional application No. 61/154,171, filed on Feb. 20, 2009.

(30) Foreign Application Priority Data

Aug. 1, 2008 (IN) ............................ 1854/CHE/2008
Dec. 3, 2008 (IN) ............................ 3053/CHE/2008

(51) Int. Cl.
- *C07H 19/12* (2006.01)
- *C07H 17/02* (2006.01)
- *A61K 31/53* (2006.01)
- *C07D 405/04* (2006.01)
- *C07H 13/12* (2006.01)

(52) U.S. Cl.
CPC ................ *C07H 17/02* (2013.01); *A61K 31/53* (2013.01); *C07D 405/04* (2013.01); *C07H 13/12* (2013.01); *C07H 19/12* (2013.01)

(58) Field of Classification Search
CPC ...... A61K 31/53; C07D 405/04; C07H 17/02; C07H 19/12; C07H 13/12
See application file for complete search history.

(56) References Cited

U.S. PATENT DOCUMENTS

| 3,350,388 | A | 10/1967 | Sorm |
|---|---|---|---|
| 3,817,980 | A | 6/1974 | Vorbruggen et al. |
| 4,082,911 | A | 4/1978 | Vorbruggen |
| 4,209,613 | A | 6/1980 | Vorbruggen |
| 6,887,855 | B2 | 5/2005 | Ionescu et al. |
| 6,943,249 | B2 | 9/2005 | Ionescu et al. |
| 7,038,038 | B2 | 5/2006 | Ionescu et al. |
| 7,078,518 | B2 | 7/2006 | Ionescu et al. |
| 7,192,781 | B2 * | 3/2007 | Luna et al. ...................... 436/98 |
| 7,700,770 | B2 * | 4/2010 | Ionescu et al. ................ 544/212 |
| 7,772,199 | B2 * | 8/2010 | Ionescu et al. .................. 514/43 |
| 7,858,774 | B2 * | 12/2010 | Ionescu et al. ............... 536/55.3 |
| 8,058,424 | B2 * | 11/2011 | Ionescu et al. ............... 536/55.3 |
| 8,158,605 | B2 | 4/2012 | Silverman et al. |
| 8,703,932 | B2 * | 4/2014 | Cherukupally et al. ..... 536/28.3 |
| 2005/0227367 | A1 | 10/2005 | Luna et al. |

OTHER PUBLICATIONS (R) Sigma Catalog, Biochemical and Reagents for Life Science Research, St. Louis, MO, 2000-2001, only p. 143 supplied, see col. 1, entry A 2385.*

Winkley and Robins, "Direct Glycosylation of 1,3,5-Triazinones. A New Approach to the Synthesis of the Nucleoside Antibiotic 5-Azacytidine (4-Amino-1-β-D-ribofuranosyl-1,3,5-triazin-2-one) and Related Derivatives", The Journal of Organic Chemistry, Feb. 1970, pp. 491-495, vol. 35—issue No. 2.

Niedballa and Vorbruggen, "A General Synthesis of N-Glycosides. V.1,2 Synthesis of 5-Azacytidines", J. Org. Chem., 1974, pp. 3672-3674, vol. 39—issue No. 25.

Beisler, "Isolation, Characterization and Properties of a Labile Hydrolysis Product of the Antitumor Nucleoside, 5-Azacytidine", Journal of Medicinal Chemistry, 1978, pp. 204-208, vol. 21—issue No. 2, The American Chemical Society.

(R) Sigma Catalog, Biochemical and Reagents for Life Science Research, 2000-2001, p. 143, col. 1, entry A 2385, St. Louis, MO.

International Search Report dated Mar. 18, 2010 for corresponding International Patent Application No. PCT/US2009/052376.

Non-Final Office Action for U.S. Appl. No. 13/016,335 mailed by the USPTO on Apr. 24, 2012.

Final Office Action for U.S. Appl. No. 13/016,335 mailed by the USPTO on Apr. 29, 2013.

* cited by examiner

*Primary Examiner* — Lawrence E Crane

(74) *Attorney, Agent, or Firm* — Pergament & Cepeda LLP; Milagros A. Cepeda; Edward D. Pergament

(57) ABSTRACT

The present invention relates to process for the preparation of azacitidine and its crystalline forms.

10 Claims, 4 Drawing Sheets

AZACITIDINE PROCESS AND POLYMORPHS

This application is a Continuation of U.S. patent application Ser. No. 13/016,335, filed on Jan. 28, 2011, which is a Continuation of International Application No. PCT/US2009/052376, filed Jul. 31, 2009, which claims priority to U.S. Provisional Application Nos. 61/102,064, filed Oct. 2, 2008, and 61/154,171, filed on Feb. 20, 2009 and Indian Provisional Applications 1854/CHE/2008, filed on Aug. 1, 2008, and 3053/CHE/2008, filed on Dec. 3, 3008, all of which are hereby incorporated by reference in their entireties.

INTRODUCTION

The present application relates to processes for the preparation of azacitidine. Further, it also relates to processes for the preparation of crystalline Form I and a mixture of crystalline Forms I and II of azacitidine.

The drug having the adopted name "azacitidine" has a chemical name 4-amino-1-β-D-ribofuranosyl-S-triazin-2 (1H)-one, is also known as 5-azacytidine, and is structurally represented by Formula I.

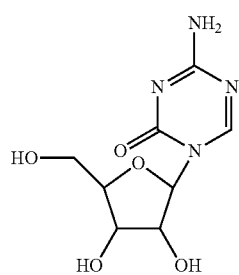

Formula I

Azacitidine, a pyrimidine nucleoside analog of cytidine, is indicated for the treatment of patients with myelodysplastic syndrome, refractory anemia with excess blasts, refractory anemia with excess blasts in transformation and chronic myelomonocytic leukemia.

The drug is commercially marketed by Pharmion Corporation under the brand name VIDAZA® in the form of a sterile lyophilized powder for injection containing 100 mg of azacitidine and 100 mg of mannitol.

U.S. Pat. No. 3,350,388 discloses a process for preparing 5-Azacytidine which involves reacting 1-(2,3,5-tri-O-acetyl-beta-D-ribofuranosyl)-4-methyl-mercapto-2-oxo-1,2-dihydro-1,3,5-triazine with dry ammonia in anhydrous methanol.

U.S. Pat. No. 3,819,780 discloses a process which involves reacting a bis-silyl compound of 5-Azacytosine with 1-O-acetyl-2,3,5-tri-O-benzoyl-beta-D-ribofuranose in the presence of $SnCl_4$ and absolute dichloroethane to give 5-azacytidine tribenzoate, which is further reacted with methanolic ammonia to give 5-azacytidine.

U.S. Pat. No. 4,082,911 discloses a process for preparing a nucleoside containing principally the beta derivative of sugar by reaction of a silylated organic base convertible to a nucleoside with a 1-O-acyl, 1-O-alkyl or 1-halo derivative of a masked sugar in the presence of a catalyst consisting essentially of a trialkylsilyl ester of an esterifiable mineral acid or of a strong sulfonic acid.

U.S. Pat. No. 4,209,613 discloses a process for preparing a nucleoside, which involves silylating the corresponding nucleoside base and reacting the sugar derivative in a single step in the presence of a Lewis acid catalyst.

M. W. Winkley et al., "Direct Glycosylation of 1,3,5-Triazinones, A New Approach to the Synthesis of the Nucleoside Antibiotic 5-Azacytidine (4-Amino-1-β-D-ribofuranosyl-1, 3,5-triazin-2-one) and Related Derivatives," *Journal of Organic Chemistry*, 35(2), pp. 491-495, 1970 discloses a process for the preparation of azacitidine, which involves the condensation of trimethylsilyl derivative of 5-azacytosine with tri-O-acetyl-D-ribofuranosyl bromide in dry acetonitrile followed by deprotection of the protecting groups with methanolic ammonia solution.

U. Niedballa et al., "A General Synthesis of N-Glycosides. V, Synthesis of 5-Azacytidines," *Journal of Organic Chemistry*, 39(25), pp. 3672-3674, 1974 discloses a process which involves the coupling of an acylated sugar of Formula A with silylated 5-Azacytosine of Formula B in the presence of $SnCl_4$ and 1,2-dichloroethane or acetonitrile to give a acylated nucleoside of Formula C, which is saponified using methanolic sodium methoxide to give 5-azacytidine. The process is depicted in Scheme 1 below.

Scheme 1

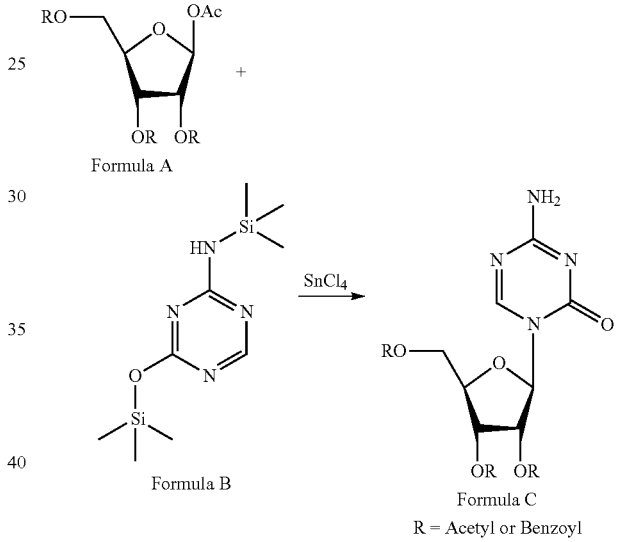

R = Acetyl or Benzoyl

The work-up of the coupling reaction involves quenching of the reaction mass with ice cold water, saturated sodium bicarbonate solution, followed by separation of the organic layer and evaporation to give a compound of Formula C in the form of a residue.

*Journal of Medicinal Chemistry* 21, 204 (1978) discloses that 5-Azacytidine has a particular sensitivity to water and aqueous formulations of 5-azacytidine lead to the formation of degradation products resulting from hydrolysis of the triazine ring.

U.S. Pat. No. 7,038,038 and U.S. Patent Application Publication No. 2006/0247432 A1 disclose a process for preparing azacitidine, wherein the process involves the reaction of 5-azacytosine with a silylating reagent to give bis silylated cytosine (Formula II), which is coupled with 1,2,3,4-tetra-O-acyl-β-D-ribofuranose (Formula III) in the presence of trimethylsilyl trifluoromethane sulfonate (TMS-triflate) and dichloromethane, acetonitrile or 1,2-dichloroethane to produce 1-(2,3,5-tri-O-acyl-beta-D-ribofuranosyl)-4-[(substitutedsilyl)amino]-1,3,5-triazin-2(1H)-one (Formula IV) which is further reacted with sodium methoxide in methanol for the removal of the silyl and acyl protecting groups, as depicted in Scheme 2.

3

Scheme 2

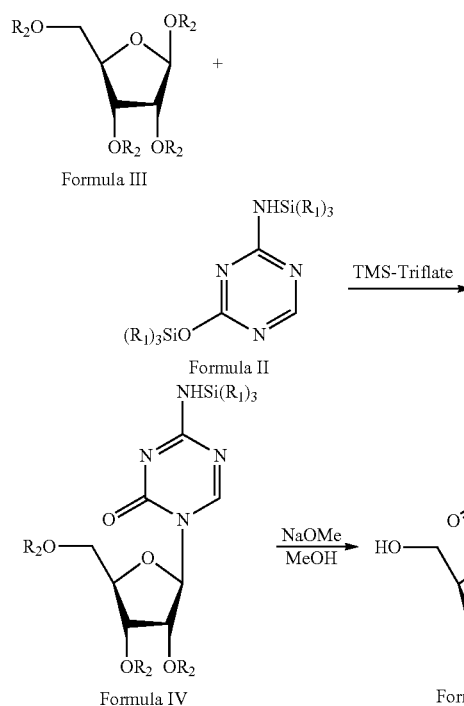

Formula III

Formula II

Formula IV wherein $R_1$ is a optionally substituted $C_1$-$C_{20}$ alkyl group
$R_2$ is a optionally substituted $C_1$-$C_{20}$ acyl group The inventors of the present application have found that conducting the glycosylation reaction according to the processes disclosed in the publications using $SnCl_4$ (in the presence of solvents like acetonitrile, dichloromethane or dichloroethane) as well as TMS-triflate may result in processing difficulties like the formation of emulsions and colloids during work up of the reaction mixtures or result in non compliance to Pharmacopeial requirements like the higher heavy metal contents, sulphated ash contents or the like.

U.S. Pat. No. 6,887,855 discloses crystalline forms Form IV, V, VII and VIII of 5-azacytidine. According to the US '855 patent, Forms I, II, III, VI, a mixture of Forms I and II, and a mixture of Form I and VI are found in the retained samples of 5-azacytidine.

U.S. Pat. No. 6,943,249 discloses a process for isolating crystalline Form I of 5-azacytidine, substantially free of other forms, comprising recrystallizing 5-Azacytidine from a solvent mixture comprising at least one primary solvent selected from dimethylsulfoxide, dimethylformamide, dimethylacetamide, and N-methylpyrrolidinone; and at least one co-solvent selected from the group consisting of $C_2$-$C_5$ alcohols, aliphatic ketones and alkyl cyanides.

U.S. Pat. No. 7,078,518 discloses methods of preparing Form IV, V, and VIII of 5-azacytidine substantially free of other forms; and a method of preparing a mixed phase of Form I and Form VII of 5-azacytidine.

U.S. Patent Application Publication No. 2005/0272675 A1 discloses a method for isolating crystalline Form I of 5-azacytidine substantially free of other forms, the method comprising recrystallizing 5-azacytidine from a solvent mixture comprising dimethylsulfoxide and methanol.

There exists a need for a simple and efficient process for the preparation of 5-azacytidine, which is amenable to scale-up. Further, there also exists a need for simple, controlled procedure for the preparation of crystalline Form I or mixture of crystalline Form I and II of 5-azacytidine.

SUMMARY

In aspects, the present application provides processes for the preparation of azacitidine.

Further aspects provide processes for the preparation of crystalline Form I and a mixture of crystalline Forms I and II of azacitidine.

An aspect of the present application provides processes for the preparation of azacitidine, an embodiment comprising:

a) silylating 5-azacytosine to give a compound of Formula II,

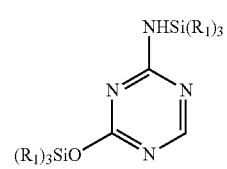

wherein $R_1$ is an optionally substituted $C_1$-$C_{10}$ alkyl group;

b) coupling the compound of Formula II with a compound of Formula III:

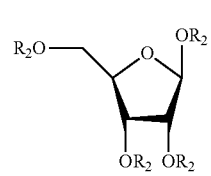

wherein $R_2$, is an optionally substituted acyl or aroyl group, in the presence of a coupling agent, which may be a non-Lewis acid compound or a metallic Lewis acid, and an organic solvent to provide the compound of Formula V; and

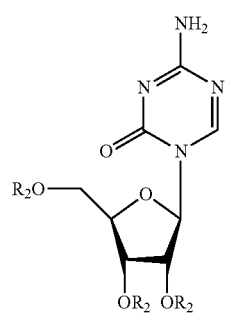

c) converting the compound of Formula V to azacitidine.

Another aspect of the present application provides process for the preparation of azacitidine, an embodiment comprising:

a) silylating 5-azacytosine to give a compound of Formula II,

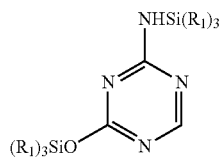

wherein $R_1$ is an optionally substituted $C_1$-$C_{10}$ alkyl group;

b) coupling the compound of Formula II with a compound of Formula III,

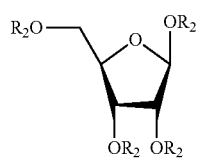

wherein $R_2$, is an optionally substituted acyl or aroyl group, in the presence of TMS-triflate and an ester solvent to provide the compound of Formula V; and

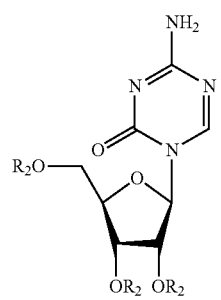

c) converting the compound of Formula V to azacitidine.

In another aspect, the present application provides processes for the preparation of crystalline Form I of azacitidine, a process comprising:

a) providing a solution of azacitidine in an organic solvent;
b) crystallizing a solid from solution of step a); and
c) isolating the obtained solid.

In an embodiment, the present application provides processes for the preparation of crystalline Form I of azacitidine, a process comprising crystallizing azacitidine from a solvent mixture comprising dimethylsulfoxide and toluene, or N,N-dimethylformamide and toluene.

In another embodiment, the present application provides processes for the preparation of crystalline Form I of azacitidine, a process comprising crystallizing azacitidine from a solvent mixture comprising an organic acid and an anti-solvent. An anti-solvent may a $C_1$-$C_5$ alcohol, an ester, an aliphatic ketone, an alkyl cyanide, a hydrocarbon, or a halogenated solvent.

In yet another aspect, the present application provides processes for the preparation of a mixture of crystalline Forms I and II of azacitidine, a process comprising:

a) providing a solution of azacitidine in N-methylpyrrolidinone;
b) crystallizing a solid by adding an alcohol; and
c) isolating the obtained solid.

DETAILED DESCRIPTION

Figure 1:
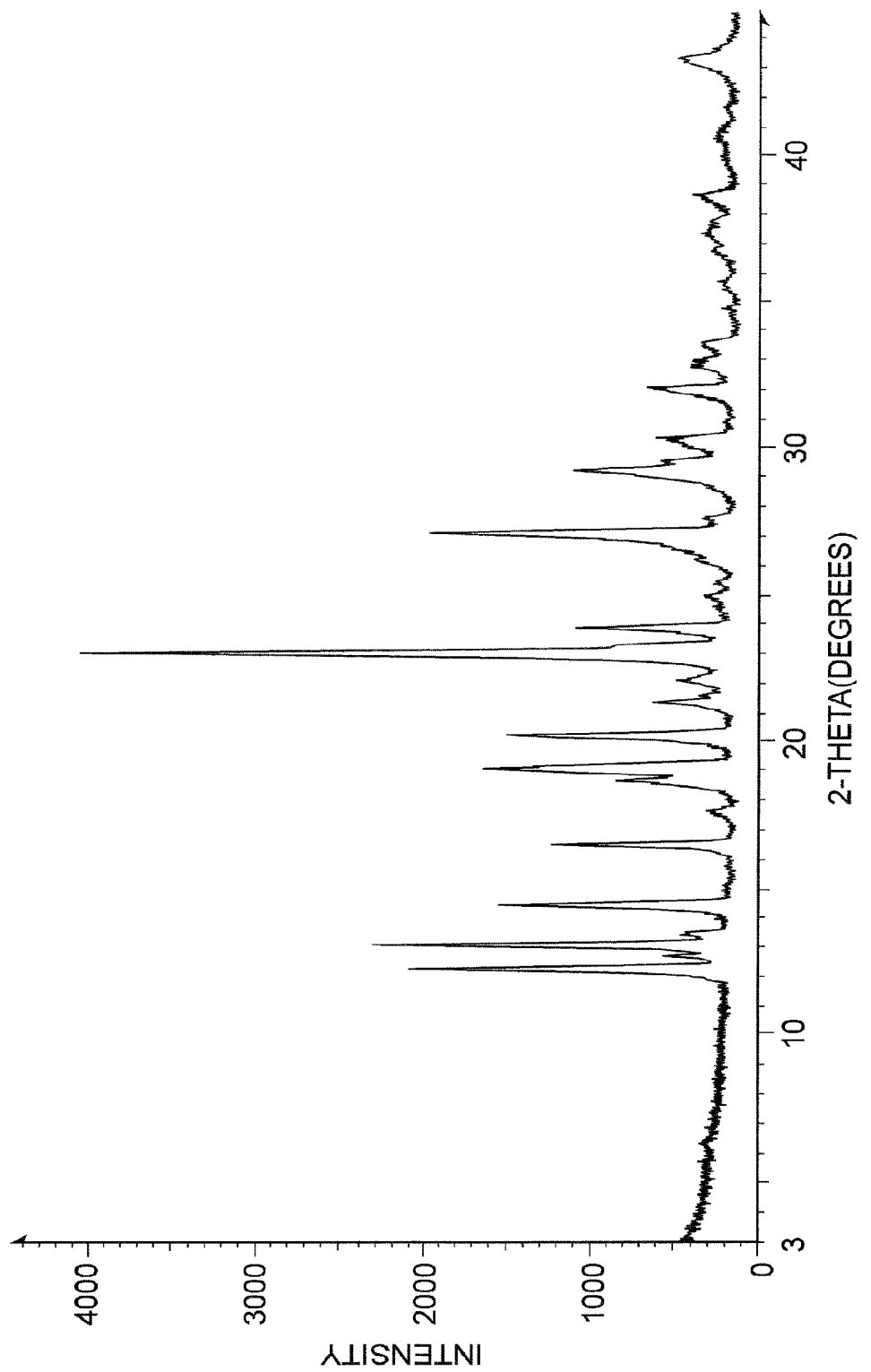
FIG. 1 is an example of an X-ray powder diffraction (XRPD) pattern of a mixture of crystalline Forms I and II of azacitidine, obtained according to Example 8.

In aspects, the present application provides processes for the preparation of azacitidine.

Further aspects provide processes for the preparation of crystalline Form I and a mixture of crystalline Forms I and II of azacitidine.

An aspect of the present application provides processes for the preparation of azacitidine, an embodiment comprising:

a) silylating 5-azacytosine to give a compound of Formula II,

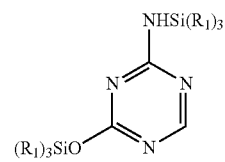

wherein $R_1$ is an optionally substituted $C_1$-$C_{10}$ alkyl group;

b) coupling the compound of Formula II with a compound of Formula III,

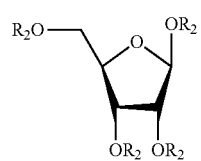

wherein $R_2$ is an optionally substituted acyl or aroyl group, in the presence of a coupling agent, which may be a non-Lewis acid compound or a metallic-Lewis acid, and an organic solvent to provide the compound of Formula V; and

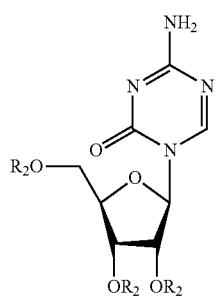

V c) converting the compound of Formula V to azacitidine.

The steps for this process are separately described below.

Step a).

The compound of Formula II may be obtained by reacting 5-azacytosine with a silylating agent, optionally in the presence of a catalyst.

The silylating agents that may be used in the processes of the present application include, but are not limited to, hexamethyldisilazane, trimethylsilyl chloride, t-butyldimethylsilyl chloride, and mixtures thereof.

The catalysts that may be used include, but are not limited to, ammonium sulphate, $Al(HSO_4)_3$, and ammonium phosphate.

The amounts of silylating agent that may be used may range from about 1 to about 2.5 molar equivalents, per molar equivalent of 5-azacytosine. In embodiments, about 2 moles, per molar equivalent of 5-azacytosine, are used. If an excess molar equivalent of the silylating agent is used, it may be removed by distillation, optionally under vacuum.

The silylation reaction may be carried out in the presence or absence of an organic solvent. A silylating agent in excess molar ratio may also be utilized as a solvent.

Organic solvents that may be used in the silylation reaction include, but are not limited to: aromatic hydrocarbons such as toluene, xylene, and the like; and nitriles such as acetonitrile, propionitrile, and the like.

The silylation reaction may be carried out at temperatures up to the boiling point of the solvent, when an organic solvent is used. In embodiments, the reaction may be carried out at temperatures about 75-85° C.

The silylation reaction may also be carried out at temperatures about 90° C. to about 135° C. when a silylating agent is utilized as a solvent. In embodiments, it may be carried out at temperatures about 120-135° C.

The compound of Formula II may be used in situ for coupling with the compound of Formula III. Optionally, the compound of Formula II may be isolated before coupling with the compound of Formula III.

Step b).

The compound of Formula III may be obtained by methods known in the art. $R_2$ is a hydroxyl-protecting group, such as, but not limited to, acyl and aroyl groups. The alkyl or aryl groups of the acyl or aroyl, respectively, may optionally be substituted. In embodiments, $R_2$ may be acetyl or benzoyl.

Embodiments of the present application provide the coupling of a compound of Formula II with a compound of Formula III, involving one of the following processes:

Process 1: using a non-Lewis acid compound in the presence of an organic solvent.

Process 2: using a metallic Lewis acid in the presence of an ester solvent.

Process 1.

A non-Lewis acid can be used as a catalyst for the coupling of compounds of Formulae II and III in the preparation of azacitidine.

Embodiments of the present application provide the coupling of a compound of Formula II with a compound of Formula III in the presence of a non-Lewis acid and an organic solvent.

The amounts of a compound of Formula III used for coupling may range from about 0.9 to about 1.1 molar equivalents, per molar equivalent of 5-azacytosine used in step a).

Non-Lewis acid compounds that may be used for coupling include, but are not limited to, trifluoromethanesulfonic acid (triflic acid), trichloromethanesulfonic acid and methanesulfonic acid. In embodiments, triflic acid is used as a coupling agent.

The amounts of coupling agent that may be used may range from about 1 to about 1.5 molar equivalents, per molar equivalent of 5-azacytosine. In embodiments, about 1.2 moles, per molar equivalent of 5-azacytosine, are used.

The organic solvents that may be used in the coupling step include, but are not limited to: esters such as ethyl acetate, n-propyl acetate, n-butyl acetate, and t-butyl acetate; halogenated hydrocarbons such as dichloromethane, 1,2-dichloroethane, chloroform, and carbon tetrachloride; and nitriles such as acetonitrile and propionitrile. The coupling reaction may be conducted at temperatures of about 0° C. to about 60° C., or the boiling point of the solvent used. In embodiments, the reaction may be conducted at temperatures of about 40° C. to about 50° C.

In embodiments, after completion of the reaction, the reaction mixture may be optionally distilled under vacuum, and diluted with a water immiscible organic solvent. Optionally water may be added to obtain a biphasic medium, followed by separation of the organic layer. The obtained reaction mass may optionally be diluted with an organic solvent or the solvent used in the coupling step, and the reaction mixture may be quenched by the addition of an acid or base, then the organic layer is separated and concentrated under vacuum, or the product may be isolated by methods known in the art to give the compound of Formula V.

Suitable acids that may be used include, but are not limited to, hydrochloric, hydrobromic, and hydrofluoric acids, and the like, as a solution in water. Suitable bases that may be used include, but are not limited to, sodium carbonate, sodium bicarbonate, potassium carbonate, potassium bicarbonate, and mixtures thereof, either as a solid or as a solution in water. In embodiments, sodium carbonate, sodium bicarbonate, or a mixture thereof is used for quenching the reaction mass.

The pharmacopeial upper limit for inorganic impurities, called "residue on ignition" (ROI), in a final active pharmaceutical ingredient is a small amount. Since silicon is a metalloid, which will be reflected in a residue on ignition test, silicon-containing groups have to be removed to meet the specification. However, processes of the present application involve the use of TMS-triflate as a coupling agent and this results in a ROI of less than 0.5% w/w in the azacitidine obtained. A procedure for performing this analysis is provided as Test 281 "Residue on Ignition," in *United States Pharmacopeia* 29, United States Pharmacopeial Convention, Inc., Rockville, Md., 2005.

The inventors of the present application have found that use of triflic acid as the coupling agent along with the process conditions of the present application results in the azacitidine having sulphated ash content meeting the pharmacopeial requirements.

Further, quenching the reaction mass by using an acid can also reduce the sulphated ash in azacitidine to less than 0.1% w/w, or to less than about 0.05% w/w.

Further, the inventors of the present application have found that quenching the reaction mass using solid sodium carbonate or sodium bicarbonate can reduce the degradation of the compound of Formula V, as compared to the use of a saturated solution of sodium carbonate or sodium bicarbonate, or a mixture of both. In embodiments, solid sodium carbonate is used for quenching the reaction mass.

Optionally, the reaction mixture may be quenched with a basic ion exchange water insoluble resin. The resins that may be used in the process of the present application include, but are not limited to, food grade weak anion exchangers, e.g., Tulsion™ A-2X-MP resin, Thermax™ (A-23, A-32, A-36 Mp), Amberlite™ IRA 67, IRA 96, and IRA 900, Amberlyst™ A-26 OH and A-21 (from Rohm & Haas); and resins made of basic polymers, e.g., polystyrene copolymers with amine functional groups for interaction. The resin may have particle sizes from about 75 to 1200 µm and ion exchange capacities from about 1.25 to 3.1 mg/mL.

In embodiments, the reaction mass is treated with aqueous HCl, followed by treatment with sodium carbonate solution, separation of the organic layer, and concentrating under vacuum to give the compound of Formula V.

Process 2.

The inventors of the present application found that conducting the coupling reaction in the presence of a metallic Lewis acid, optionally in an ester solvent, not only facilitates the completion of the reaction, but also assists in the easy reaction work-up, resulting in improved purity of azacitidine.

An embodiment of the present application provides the coupling of a compound of Formula II with a compound of Formula III, using a metallic Lewis acid, in the presence of an ester solvent.

The amounts of a compound of Formula III used for coupling may range from about 0.95 to about 1.1 molar equivalents, per molar equivalent of 5-azacytosine used in step a).

Metallic Lewis acids that may be used for coupling include, but are not limited to, stannic chloride ($SnCl_4$), $TiCl_4$, $ZnCl_2$, bismuth triflate [$Bi(OTf)_3$], boron trifluoride etherate ($BF_3OEt_2$), AgOTf, $AgClO_4$, $FeCl_3$, $AlCl_3$ and $SbCl_5$. In an embodiment, $SnCl_4$ is used as a coupling agent.

The amount of coupling agent that may be used may range from about 1 to about 1.5 molar equivalents, per molar equivalent of 5-azacytosine. In an embodiment, about 1.2 moles per molar equivalent of 5-azacytosine is used.

Ester solvents that may be used in the coupling step include, but are not limited to, ethyl acetate, n-propyl acetate, n-butyl acetate, and t-butyl acetate.

The coupling reaction may be carried at temperatures about 0° C. to about 35° C.

After completion of the reaction, the product may be isolated or the work-up of the reaction mass may be carried out as described in Process 1.

Alternatively, the quenched reaction mass of either of Process 1 or Process 2 may be optionally filtered before the organic layer is separated. The aqueous layer optionally may be extracted with a water-immiscible organic solvent, such as the solvent used in the coupling step. The combined organic layer may be optionally washed with saturated sodium bicarbonate solution or water. The washing may be carried out by vigorous stirring of the organic layer with aqueous sodium carbonate, or water, for about 10-15 minutes and separating the aqueous layer, which may be discarded. Optionally, the washing process may be repeated, such as 1 to 3 more times.

The organic layer obtained by any of the above processes of the invention may further be concentrated, either completely or to a minimum volume, under vacuum, to give a residue or a concentrated solution containing a compound of Formula V. The concentrated solution or residue may be optionally cooled to a temperature of about 25° C. to about 35° C.

Optionally, the solvent present in the concentrated solution of Formula V may be replaced with an alcohol. An example of a method of solvent replacement is by co-distillation. The alcohols that can be used for this purpose include, but are not limited to, $C_1$-$C_4$ alcohols such as methanol, ethanol, isopropanol, and mixtures thereof.

Step c).

The compound of Formula V obtained in step b) is converted to azacitidine of Formula I by the deprotection of the acyl or aroyl protecting groups in the presence of a suitable base, or by sparging with ammonia gas.

Suitable bases that may be used for the deprotection of the acyl or aroyl protecting groups include, but are not limited to: alkali metal hydroxides such as sodium hydroxide and potassium hydroxide; metal alkoxides such as sodium methoxide and sodium ethoxide; alkali metal carbonates such as sodium carbonate and potassium carbonate; and organic bases such as diethylamine, n-butyl amine, propyl amine, and the like.

The solvents that may be used in step c) include, but are not limited to, $C_1$-$C_4$ alcohols such as methanol, ethanol, n-propanol, and mixtures thereof.

Temperatures at which the reaction may be carried out range from about 0° C. to about 65° C., or the boiling point of the solvent used. In embodiments, the reaction may be carried at temperatures about 55° C. to about 65° C.

The isolation of the product obtained may be carried out using methods known in the art.

The azacitidine thus obtained may be dried. Drying may be suitably carried out in equipment such as a tray dryer, vacuum oven, air oven, fluidized bed dryer, spin flash dryer, flash dryer, and the like. The drying may be carried out at temperatures about 45° C. to about 85° C., or at about 70-80° C., optionally under reduced pressure. The drying may be carried out for any time periods necessary for obtaining a product with desired purity, such as from about 1 to about 25 hours, or longer.

A process for the preparation of azacitidine according to the above aspect of the present application is schematically summarized in Scheme 3.

Scheme 3

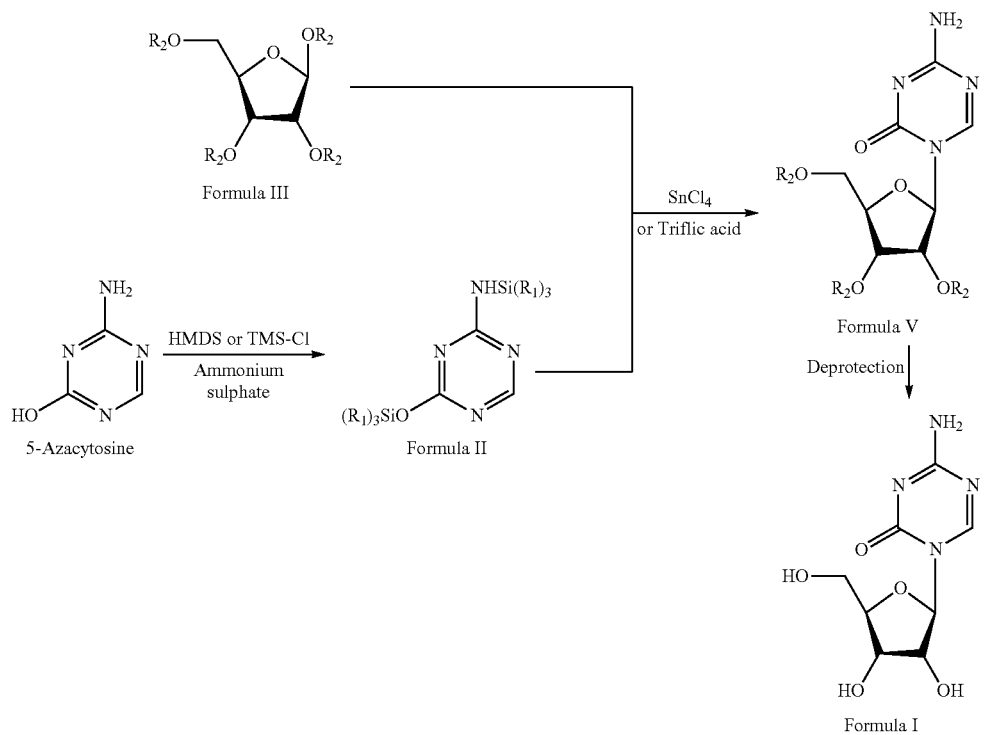

An aspect of the present application provides processes for the preparation of azacitidine, an embodiment comprising:

a) silylating 5-azacytosine to give a compound of Formula II,

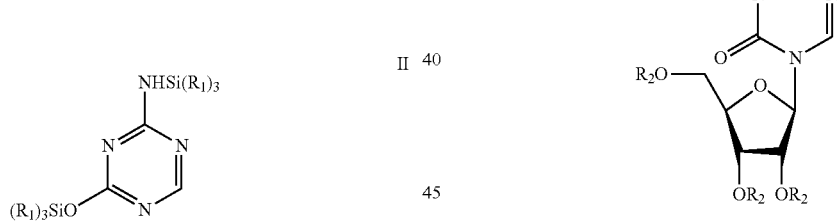

wherein $R_1$ is an optionally substituted $C_1$-$C_{10}$ alkyl group;

b) coupling the compound of Formula II with a compound of Formula III,

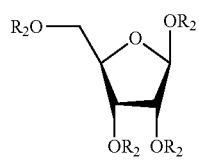

wherein $R_2$, is an optionally substituted acyl or aroyl group, in the presence of a TMS-triflate and an ester solvent to provide the compound of Formula V; and c) converting the compound of Formula V to Azacitidine.

The steps for this process are separately described below.

Step a) of the process may be carried out according to the process disclosed in the above-described aspect of the present application.

Step b) involves the coupling of a compound of Formula II with a compound of Formula III.

The compound of Formula III may be obtained by methods known in the art. $R_2$ is a hydroxyl protecting group, such as, but not limited to, acyl and aroyl. The alkyl or aryl groups of the acyl or aroyl, respectively, may optionally be substituted. In embodiments, $R_2$ may be acetyl or benzoyl.

An embodiment of the present application provides the coupling of a compound of Formula II with a compound of Formula III in the presence of TMS-triflate and an organic solvent.

The amount of a compound of Formula III used for coupling may range from about 0.95 to about 1.2 molar equivalents, per molar equivalent of 5-azacytosine used in step a).

The amount of TMS-triflate as a coupling agent may range from about 1 to about 1.5 molar equivalents, per molar equivalent of 5-azacytosine. In an embodiment, about 1.2 moles per molar equivalent of 5-azacytosine may be used.

The ester solvents that may be used in the coupling step include, but are not limited to, ethyl acetate, n-propyl acetate, n-butyl acetate, t-butyl acetate, and mixtures thereof.

The inventors of the present application have found that the use of an ester solvent in the coupling step not only facilitates the reaction completion, but also assists in easy work-up.

The coupling reaction may be carried at temperatures about 0° C. to about 50° C.

After completion of the reaction, the reaction mixture may be optionally distilled under vacuum. The obtained reaction mass may optionally be diluted with an organic solvent or the solvent used in the coupling step and the reaction mixture may be quenched by the addition of a base such as sodium carbonate, sodium bicarbonate, potassium carbonate, potassium bicarbonate, and mixtures thereof, either as a solid or as a solution in water, and the organic layer is separated. In embodiments, solid sodium carbonate or sodium bicarbonate is used for quenching the reaction mass. Optionally, the reaction mixture may also be quenched with a basic ion exchange water insoluble resin.

The quenched reaction mass may be filtered before the organic layer is separated. The aqueous layer optionally may be extracted with a water-immiscible organic solvent, such as the solvent used in the coupling step. The organic layer obtained may be concentrated either completely or to a minimum volume under vacuum to give a residue or a concentrated solution of a compound of Formula V. The concentrated solution or residue may be optionally cooled to a temperature of about 25° C. to about 35° C.

Optionally, the solvent present in the concentrated solution of Formula V may be replaced with an alcohol. An example of a method of solvent replacement is by co-distillation. The alcohols that can be used for this purpose include, but are not limited to, $C_1$-$C_4$ alcohols such as methanol, ethanol, isopropanol, and mixtures thereof.

Step c)

The compound of Formula V obtained in step b) is converted to azacitidine of Formula I by the deprotection of the acyl or aroyl protecting groups in the presence of a base, or by sparging with ammonia gas.

Suitable bases that may be used for the deprotection of the acyl or aroyl protecting groups include, but are not limited to: alkali metal hydroxides such as sodium hydroxide and potassium hydroxide; metal alkoxides such as sodium methoxide and sodium ethoxide; alkali metal carbonates such as sodium carbonate and potassium carbonate; and organic bases such as diethylamine, butylamine, propylamine, and the like.

Solvents that may be used in step c) include, but are not limited to, $C_1$-$C_4$ alcohols such as methanol, ethanol, isopropanol, and mixtures thereof.

The temperatures at which the reaction may be carried out range from about 0° C. to about 65° C. In embodiments, the reaction may be carried at temperatures of about 0° C. to about 5° C.

The isolation of the product obtained any of the processes of the present invention may be carried out using methods known in the art or by a process as described herein.

Azacitidine that is obtained may be optionally purified using techniques known in the art, such as column purification, crystallization, or slurrying in a suitable solvent or mixture of solvents.

An embodiment of the present application includes the use of solvent mixtures comprising: dimethylsulfoxide and toluene; N,N-dimethylformamide and toluene; and N-methylpyrrolidinone and methanol; for the purification of azacitidine.

Azacitidine obtained by the process of the present application typically has a purity not less than about 97% by weight, as determined by high performance liquid chromatography (HPLC).

In an aspect, the present application provides processes for the preparation of crystalline Form I of Azacitidine, an embodiment comprising:

a) providing a solution of azacitidine in an organic solvent;
b) crystallizing a solid from solution of step a); and
c) isolating the obtained solid.

The steps for the process for the preparation of crystalline Form I of azacitidine of the present application are described below.

Step a).

The solution of azacitidine may be provided by the dissolution of azacitidine in an organic solvent, or may be obtained from a process by which the compound is prepared. Any form of azacitidine, such as any crystalline or amorphous form of azacitidine, obtained by any method; is acceptable for providing the solution.

Organic solvents that may be used for providing the solution of azacitidine include, but are not limited to, dimethylsulfoxide, N,N-dimethylformamide, and organic acids.

Suitable organic acids that may be used include, but are not limited to, formic acid, acetic acid, and the like.

The concentration of azacitidine in the solution is not critical as long as sufficient solvent is employed to ensure total dissolution. The amount of solvent employed is typically kept to a minimum so as to avoid excessive product loss during crystallization and isolation. The quantities of solvents used for providing solutions of azacitidine may range from about 3 times to about 30 times, or more, the weight of azacitidine.

The solution may be prepared by combining azacitidine with the solvent chosen at room temperature, and optionally heating to the desired temperature of dissolution, or by adding azacitidine to a pre-heated solvent.

The solution may be prepared at temperatures ranging from about 20° C. to 100° C., or the boiling point of the solvent chosen. Depending on the solvent and quantity used, solute may dissolve at 25 to 35° C., or the solution may need to be heated to higher, including reflux, temperatures.

The solution may optionally be filtered by passing through paper, glass fiber, or other membrane material, or a bed of clarifying agent such as Hyflow (flux-calcined diatomaceous earth). Depending upon the equipment used and the concentration and temperature of the solution, the filtration apparatus may need to be heated to avoid premature crystallization.

Step b).

Crystallizing a solid from the solution of step a) may be performed by methods such as cooling, partial removal of the solvent from the mixture, seeding, adding an anti-solvent to the reaction mixture, or any combination thereof.

In an embodiment, the crystallization may be carried out by combining the solution of step a) with a suitable anti-solvent.

Adding the solution of step a) to the anti-solvent, or adding an anti-solvent to the solution of step a), to initiate crystallization process are both within the scope of the present application.

In embodiments, toluene is used as an anti-solvent when the solvent used for the dissolution of azacitidine is dimethylsulfoxide or dimethylformamide.

In embodiments, an ester is used as an anti-solvent, when an organic acid is used as the dissolution solvent. For example, ethyl acetate can be used as an anti-solvent.

The azacitidine solution can be combined with the desired anti-solvent at temperatures ranging from about 20° C. to 100° C. The combination may be carried out for a sufficient period of time, which may range from about 5 minutes to about 3 hours, or longer, to effect the desired crystallization.

The quantities of anti-solvent used for crystallization of Form I can range from about 5 to 50 times, or about 20 to 40 times with respect to the weight of azacitidine.

The temperatures at which a solid precipitates depend on the solvents and their quantities used. Optionally, the suspension obtained may be cooled to the desired temperature and may then be stirred for about 30 minutes to 5 hours, or longer, depending upon the desired extent of precipitation.

Step c).

The obtained precipitate may be isolated using conventional techniques known in the art. One skilled in the art may appreciate that there are many ways to separate a solid from the mixture, for example it may be separated by using any techniques such as filtration by gravity or by suction, centrifugation, decantation, and the like. After separation, the solid may optionally be washed with a suitable solvent.

The isolated solid may optionally be further dried. Drying may be suitably carried out in a tray dryer, vacuum oven, air oven, fluidized bed dryer, spin flash dryer, flash dryer, and the like. The drying may be carried out at temperatures about 35° C. to about 100° C., optionally under reduced pressure. The drying may be carried out for any time periods necessary for obtaining a desired purity, such as from about 1 to about 25 hours, or longer.

In an aspect, the present application provides processes for the preparation of crystalline Form I of azacitidine, an embodiment comprising crystallizing azacitidine from a solvent mixture comprising dimethylsulfoxide and toluene, or dimethylformamide and toluene.

In an aspect, the present application provides processes for the preparation of crystalline Form I of Azacitidine, an embodiment comprising crystallizing azacitidine from a solvent mixture comprising an organic acid and an anti-solvent comprising $C_1$-$C_5$ alcohols, esters, aliphatic ketones, alkyl cyanides, hydrocarbons, or halogenated solvents. In embodiments, a solvent mixture comprises formic acid and an ester.

The crystalline Form I of azacitidine obtained by the processes of the present invention may be characterized by any of its X-ray powder diffraction ("XRPD") pattern, and differential scanning calorimetry (DSC) and thermogravimetric analysis (TGA) curves. XRPD data reported herein were obtained using a Bruker Axe D8 Advance Powder X-ray Diffractometer with Cu Kα radiation.

Figure 2:
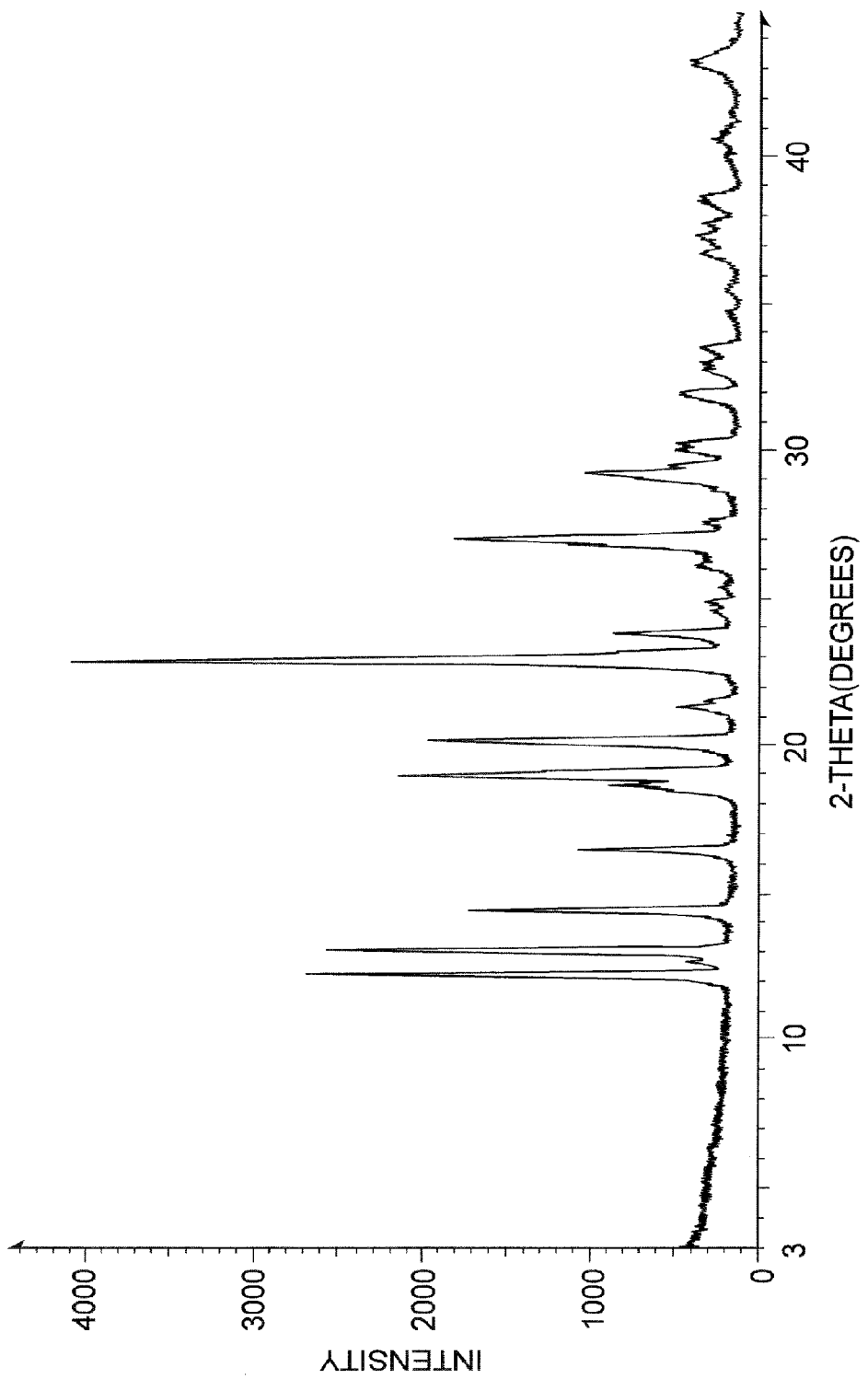
FIG. 2 is an example of an X-ray powder diffraction pattern of azacitidine crystalline Form I, obtained according to Example 5.

The crystalline Form I of azacitidine obtained by the process of the present application may be characterized by an XRPD diffraction pattern having characteristic peaks located substantially in accordance with the pattern of FIG. 2.

Crystalline azacitidine Form I of the present application may be characterized by its differential scanning calorimetry curve, having a peak onset at about 195° C. and endset at about 235° C. In an analysis, the sample was observed to decompose using a 10° C./minute heating rate and a starting temperature of 195° C. in a DSC Q1000 model instrument. Thus, the DSC event results from decomposition of azacitidine.

In yet another aspect, the present application provides processes for the preparation of a mixture of crystalline Form I and II of Azacitidine, an embodiment comprising:
a) providing a solution of azacitidine in N-methylpyrrolidinone;
b) crystallizing a solid by adding an alcohol; and
c) isolating the obtained solid.

Any form of azacitidine, such as any crystalline or amorphous form of azacitidine, obtained by any method, may be used for providing a solution of azacitidine.

The solution of azacitidine may be provided may combining azacitidine with N-methylpyrrolidinone at room temperature, optionally by heating to higher temperatures, such as about 75° C. to about 95° C., or by adding azacitidine to N-methylpyrrolidinone which is preheated, such as to temperatures about 75° C. to about 95° C.

The azacitidine solution may be combined with an alcohol at temperatures ranging from about 25° C. to 100° C., for a sufficient period of time, which may range from about 15 minutes to 2 hours, or longer, to effect the desired crystallization. In embodiments, an alcohol is added to the solution of azacitidine at temperatures about 55° C. to about 75° C., to effect the crystallization.

Alcohols useful for this purpose include, but are not limited to, $C_1$-$C_4$ alcohols such as methanol, ethanol, isopropanol, and mixtures thereof. In embodiments, methanol is used.

The suspension obtained may be optionally cooled to a desired temperature and may then be stirred for about 30 minutes to 5 hours, or longer, depending upon the desired extent of precipitation.

Separating the mixture of crystalline Forms I and II of azacitidine may be performed by a process similar to that described above for Form I.

The mixtures of crystalline Forms I and II of azacitidine obtained from the present application can be characterized by their X-ray powder diffraction ("XRPD") pattern, and differential scanning calorimetry (DSC) and thermogravimetric analysis (TGA) curves.

A mixture of crystalline Forms I and II of azacitidine obtained from the present application is characterized by an XRPD diffraction pattern comprising characteristic peaks substantially in accordance with the pattern of FIG. 1.

In yet another aspect, the present application provides pharmaceutical compositions comprising crystalline Form I or mixtures of crystalline Forms I and II of azacitidine obtained by the present application, and one or more pharmaceutically acceptable excipients.

The above processes for the preparation of crystalline Form I or the mixture of crystalline Form I and II of azacitidine may also be used as processes for the purification of azacitidine. A crystallization process can optionally be repeated to get substantially pure azacitidine having purity greater than or equal to about 99.5%, or greater than or equal to about 99.8%, by weight as determined using HPLC.

The present invention includes substantially pure azacitidine, wherein the amount of each individual process-related impurity listed in Table 1 is less than about 0.15%, or less than about 0.1%, by weight, and/or the sum of all of these impurities is less than about 0.2%, by weight.

| Impurity | Structure |
|---|---|
| A | 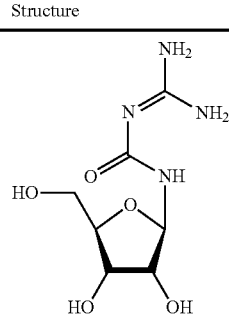 |

| Impurity | Structure |
|---|---|
| B | (structure: 4-amino-1,3,5-triazin-2(1H)-one) |
| C | (structure: guanidine-formamide with ribose: HO-CH2-ribose-NH-C(=O)-N=C(NH2)-NHCHO) |
| D | (structure: azacitidine tri-acetate: 2',3',5'-tri-O-acetyl derivative with AcO groups) |
| E | (structure: 5'-O-acetyl azacitidine with AcO at 5' and HO, OH at 2',3') |

The term "azacitidine substantially free of related impurities" as used herein shall be understood to mean azacitidine formed with little or no content of the impurities. The amount of any impurity of azacitidine resulting from the process of the preparation will be relatively minor, e.g., less than about 0.15 weight percent, or less than about 0.1 weight percent, or less than about 0.05 weight percent, of any impurity of azacitidine.

In particular, azacitidine containing less than about 0.2% by weight of total combinations of the impurities illustrated in Table 1 may be produced by processes of the present invention.

The impurities may be analyzed using various methods. Representative useful HPLC methods are described below.

Method 1.

Azacitidine may be analyzed by HPLC utilizing the following conditions:
Column: Intersil ODS 3V, 250×4.6 mm, 5.0 μm.
Column temperature: 30° C.
Injection volume: 10 μL.
Elution: Gradient.
Concentration: 0.5 mg/mL.
Buffer: Dissolve 0.02 M sodium dihydrogen phosphate monohydrate. Adjust the pH to 6.5 with dilute sodium hydroxide solution.
Mobile Phase A: Buffer.
Mobile Phase B: Mixture of buffer and acetonitrile in the volume ratio of 50:50 and degassed.
Flow rate: 0.9 mL/minute.
Wavelength of detection: 210 nm UV.
Diluent: Water.
Gradient program:

| Minutes | % Mobile Phase A | % Mobile Phase B |
|---|---|---|
| 0 | 100 | 0 |
| 8 | 100 | 0 |
| 45 | 75 | 25 |
| 60 | 50 | 50 |
| 68 | 50 | 50 |
| 68.1 | 100 | 0 |
| 75 | 100 | 0 |

Method 2.

Azacitidine may be analyzed by HPLC utilizing the following conditions:
Column: Chiral pak IA, 250×4.6 mm, 5.0 μm.
Column temperature: 27° C.
Injection volume: 10 μL.
Elution: Isocratic.
Concentration: 2.0 mg/mL.
Mobile Phase: Mixture of n-hexane and ethanol in the volume ratio of 50:50 and sonicated for 2 minutes.
Wavelength of detection: 242 nm UV.
Flow rate: 1.3 mL/minute.
Run time: 30 minutes.

Using these methods, the relative retention times (where the compound of Formula I=1) listed in Table 2 are obtained for certain process-related impurities.

TABLE 2

| Impurity | RRT |
|---|---|
| Impurity A | ~0.33 (Method I) |
| Impurity B | ~0.39 (Method I) |
| Impurity C | ~0.66 (Method II) |
| Impurity D | ~4.0 (Method I) |
| Impurity E | ~2.9 (Method I) |

Further, the processes for the purification of azacitidine as descried in the present application also help in further reducing the content sulphated ash in azacitidine to less than about 0.05% w/w, or to less than about 0.03% w/w.

Azacitidine obtained by a process of the present application may have a mean particle size d(4.3) less than about 200 μm.

In embodiments, azacitidine obtained by a process of the present application may have a mean particle size d(4.3) between about 200 μm and 10 μm.

In embodiments, azacitidine obtained by a process of the present application may have a mean particle size d(4.3) between about 170 μm and 10 μm.

In embodiments, azacitidine obtained by a process of the present application may have a particle size distribution, wherein is $D_{90}$ in the range of about 210-350 μm, $D_{50}$ is in the range of about 75-190 μm, and $D_{10}$ is in the range of about 15-65 μm.

In embodiments, azacitidine obtained by a process of the present application may have a particle size distribution, wherein $D_{90}$ is in the range of about 45-130 µm, $D_{50}$ is in the range of about 15-45 µm, and $D_{10}$ is in the range of about 2-15 µm.

Certain specific aspects and embodiments of the present application will be explained in more detail with reference to the following examples, which are provided for purposes of illustration only and should not be construed as limiting the scope of the application in any manner. Percentages are expressed by weight, unless the context clearly indicates otherwise.

EXAMPLE 1

Preparation of 2,3,5-tri-O-acetyl-5-azacytidine

Hexamethyldisilazane (94.5 mL), ammonium sulfate (1.25 g) and 5-azacytosine (25 g) were placed into a clean and dry round bottom flask and stirred. The mixture was heated to reflux at 120-134° C. and maintained for 2 to 3 hours. The mixture was distilled under vacuum to give a residue and it was allowed to cool to 25-30° C. Ethyl acetate (250 mL) was charged to the residue and stirred. 1,2,3,5-tetra-O-acetyl-beta-D-ribofuranose (67.4 g) was added and the mixture was cooled to 5-10° C. Triflic acid (23.6 mL) was slowly added over 10-30 minutes and the mixture was allowed to warm to 20-30° C. and stirred for 1-2 hours. Ethyl acetate (125 mL) and water (125 mL) were added and stirred. The organic layer was separated, washed with 20% sodium chloride solution (125 mL), and dried over sodium sulfate. The organic layer was distilled under vacuum at about 40 to 45° C. to give a residue of 2,3,5-tri-O-acetyl-5-azacytidine (50.0 g).

EXAMPLE 2

Preparation of Azacitidine

Hexamethyldisilazane (9.48 mL), ammonium sulfate (0.12 g) and 5-azacytosine (2.5 g) were placed into a clean and dry round bottom flask and stirred. The mixture was heated to reflux at 120-134° C. and maintained for 2 to 3 hours. The mixture was distilled under vacuum to give a residue and it was allowed to cool to 25-30° C. Ethyl acetate (25 mL) was charged to the residue and stirred. 1,2,3,5-tetra-O-acetyl-beta-D-ribofuranose (6.74 g) was added and the mixture was cooled to 0-10° C. Triflic acid (2.36 ml) was slowly added over 10-30 minutes and the mixture was allowed to warm to 20-35° C. and stirred for about 1 hour. Added ethyl acetate (25 mL) and added Tulsion A-2X-MP resin (30.0 g) to the mass and stirred for 20-30 minutes. The resin was removed by filtration, washed with ethyl acetate (12.5 ml) and the filtrate was distilled completely at about 40 to 45° C. to give a residue of 2,3,5-tri-O-acetyl-5-azacytidine (5.5 g).

Charged methanol (35 mL) to 2,3,5-tri-O-acetyl-5-azacytidine (5.2 g) obtained above and stirred at 25-30° C. Added 25% NaOMe solution in methanol (0.5 mL) to the mixture and stirred at 25-30° C. for 60-90 minutes. The mixture was filtered and the solid was washed with methanol (15 mL). The solid was dried at 70-80° C. for 6 hours to obtain 0.8 g of azacitidine.

EXAMPLE 3

Preparation of Azacitidine

Hexamethyldisilazane (73.9 mL) and 5-azacytosine (20 g) were placed into a clean and dry round bottom flask and stirred. Ammonium sulfate (1 g) was added and the mixture was heated to a reflux temperature of 120-134° C. and maintained for 2 to 3 hours. The mixture was cooled to 65-70° C. and distilled under reduced pressure to give a residue, which was allowed to cool to 25-30° C. Added ethyl acetate (200 mL) to the residue and stirred. 1,2,3,5-tetra-O-acetyl-beta-D-ribofuranose (53.9 g) was added and the mixture was cooled to 5-10° C., followed by the addition of $SnCl_4$ (25.1 mL) over 20 minutes. The mixture was allowed to warm to about 22-24° C., followed by stirring for 1 hour. Added sodium carbonate (110 g) and sodium bicarbonate (110 g) to the mixture and then water (60 mL) was slowly added. The mixture was filtered and washed with ethyl acetate (20 mL). The filtrate was washed with 10% $NaHCO_3$ solution (100 mL) followed by water (100 mL) and then the organic layer was dried over sodium sulfate. The organic layer was distilled completely under reduced pressure at about 40 to 45° C. to give 42.0 g of 2,3,5-tri-O-acetyl-5-azacytidine.

Added methanol (100 mL) to 2,3,5-tri-O-acetyl-5-azacytidine (22.0 g) obtained above and cooled to 5-10° C. Ammonia gas was bubbled through the mixture for about 2-3 hours and the mixture allowed to warm to about 25-30° C., and then it was stirred for 1-2 hours. The mixture was filtered and the solid washed with methanol (10 mL). The solid obtained was dried at 70-80° C. for 3 hours to obtain azacitidine.

EXAMPLE 4

Preparation of Azacitidine Form I

Combined azacitidine (10 g) and dimethylsulfoxide (50 mL), pre-heated to about 90° C., and stirred for 10 minutes. Toluene (250 mL) was added to the solution at the same temperature over 15 minutes and the mixture was stirred for 35 minutes. The suspension was cooled to about 25-30° C. and stirred for 1-2 hours. The solid was filtered, washed with toluene (30 mL) and dried for 4 hours at about 80° C. to obtain 8 g of crystalline Form I.

DSC: onset 210° C. and peak at 219° C.

TGA: 0.4077% weight loss.

EXAMPLE 5

Preparation of Azacitidine Form I

Azacitidine (10 g) was dissolved in N,N-dimethylformamide (270 mL) at about 90° C. and stirred for 10 minutes. Toluene (370 mL) was added to the solution over 20 minutes and stirred for 1 hour. The suspension was cooled to about 25-30° C. and stirred for 1 hour. The solid was filtered, washed with toluene (30 mL) and dried for 4 hours at about 80° C. to obtain 7.9 g of crystalline Form I.

XRPD diffraction pattern substantially in accordance with FIG. 2.

DSC: Onset at 214° C. and peak at 222° C.

TGA: 0.4921% weight loss.

EXAMPLE 6

Preparation of Azacitidine Form I

Azacitidine (10 g) was dissolved in formic acid (50 mL) at room temperature and stirred for 10 minutes. Ethyl acetate (335 mL) was added over 20 minutes and the mixture was stirred for 1-2 hours. The formed solid was filtered, washed with ethyl acetate (30 mL) and dried for 4 hours at about 80° C. to obtain 8 g of crystalline Form I.

DSC: Onset at 208° C. and peak at 214° C.

TGA: 1.195% weight loss.

EXAMPLE 7

Preparation of Azacitidine Form I

Azacitidine (5 g) was dissolved in formic acid (25 mL) at room temperature and stirred for 20 minutes. The solution was added to ethyl acetate (168 mL) over 30-40 minutes. The suspension was stirred for 1 hour, and the solid was filtered, washed with ethyl acetate (15 mL) and dried for 4 hours at about 80° C. to obtain 3.9 g of crystalline Form I.

DSC: Onset at 192° C. and peak at 208° C.
TGA: 1.349% weight loss.

EXAMPLE 8

Preparation of a Mixture of Azacitidine Crystalline Forms I and II

Azacitidine (10 g) was dissolved in N-methylpyrrolidinone (120 mL) at about 90° C. and stirred for 20 minutes. The solution was cooled to 65° C. and methanol (250 mL) was gradually added over 20 minutes. The mixture was stirred for 1 hour. The obtained suspension was cooled to room temperature and stirred for 1 hour. The solid was filtered, washed with methanol (30 mL) and dried for 4 hours at about 80° C. to obtain 7.9 g of the mixture.

XRPD diffraction pattern substantially in accordance with FIG. 1.

DSC: Onset at 220° C. and peak at 224° C.
TGA: 0.2798% weight loss.

EXAMPLE 9

Preparation of Azacitidine

Step a): Preparation of 5-Azacytosine

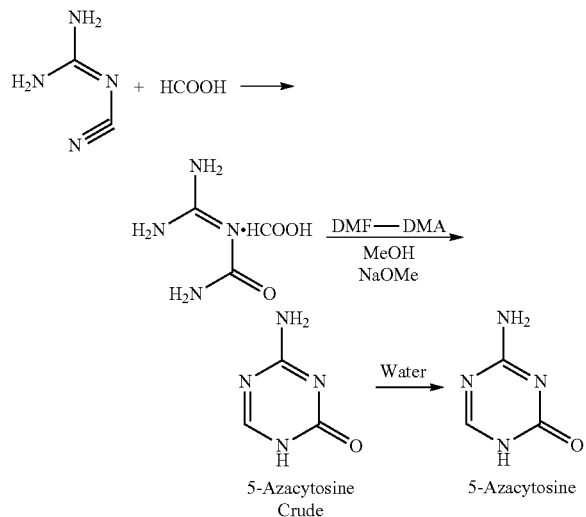

Placed cyanoguanidine (200 g) and formic acid (320 g, assay~99%) into a clean and dry round bottom flask with stirring at 28° C. The mixture was heated to 76° C. and heating was discontinued. The temperature of the mixture increased to 110° C. The mixture was maintained for 10-15 minutes at 110° C., then was cooled to 35-40° C., isopropyl alcohol (1000 mL) was added, and the mixture was maintained for 20 minutes at 28° C. Filtered the obtained solid, washed with isopropyl alcohol (200 mL) and dried for 2 hours at 70-75° C.

Charged the above obtained solid and methanol (500 ml) into a clean and dry round bottom flask at 25-35° C. Charged 25% NaOMe solution in methanol (162 g) to the mixture and stirred for 5 minutes. Added dimethylformamide dimethylacetal (270 g) to the mass slowly at 28° C. The mixture was heated to 45-50° C. and maintained for about 4 hours. Cooled the mixture to 25-35° C. and adjusted the pH to 6-7 using formic acid (~15 mL). Charged water (1000 mL) to the mixture and maintained for 15-20 minutes with stirring. Filtered the obtained precipitate, washed with a methanol-water mixture (200 mL, 1:1 by volume) and dried the solid for 3 hours at 80-90° C. Yield: 219 g.

Charged the above-obtained 5-azacytosine (219 g) and water (1800 mL) into a round bottom flask at 25-35° C. The mixture was heated to 45-50° C. and maintained for 20-30 minutes. Filtered the hot mixture, washed with water (400 mL) and dried the solid for 5 hours at 85-95° C. Yield: 190 g.

Purity by HPLC: 98.1%.

Step b): Preparation of Azacitidine

Combined hexamethyldisilazane (19 mL) and 5-azacytosine (5 g) in a round bottom flask at 28° C. Added ammonium sulfate (0.25 g) and acetonitrile (25 mL). The mixture was heated to reflux temperature at 78-80° C. and maintained for 2 hours to obtain a homogenous mixture. The mixture was distilled under vacuum at 75° C. to give a residue. Added ethyl acetate (10 mL) to the residue and distilled under vacuum at 78° C. to give a residue, which was allowed to cool to 25-35° C. Added ethyl acetate (50 mL) to the residue and stirred under a nitrogen atmosphere for dissolution. Added 1,2,3,5-tetra-O-acetyl-beta-D-ribofuranose (13.5 g) and cooled to 0-10° C. Triflic acid (4.7 mL) was slowly added over 10-30 minutes and heated to 40-45° C., then maintained for 1 hour. The mixture was distilled under vacuum below 45° C. to give a residue. Added dichloromethane (50 mL) to the residue and stirred for dissolution, then cooled the mixture to 20-30° C., added water (50 mL, pre-cooled to 10-15° C.) and stirred for 10-20 minutes. Separated the organic layer, dried with sodium sulphate and distilled under vacuum below 45° C., then further co-distilled with ethyl acetate (10 mL) to obtain a residue. Added ethyl acetate (75 mL) to the residue, maintained for 10-15 minutes, and cooled to 30-35° C. Added anhydrous sodium carbonate (5 g) to the mass and stirred for 20-30 minutes. Charged Hyflow (flux-calcined diatomaceous earth, 7.5 g) to the mixture, stirred for 20-30 minutes, filtered and washed the solid with ethyl acetate (25 mL). The filtrate was distilled under reduced pressure below 45° C. to give 10.0 g of 2,3,5-tri-O-acetyl-5-azacytidine.

Combined methanol (100 mL) with 2,3,5-tri-O-acetyl-5-azacytidine (10 g) obtained above in a round bottom flask at 28° C. and stirred. Charged 25% NaOMe solution in methanol (0.5 mL) to the mixture and stirred at 28° C. for 60-90 minutes. Filtered the mixture and washed with methanol (20 mL). The solid obtained was dried at 80-85° C. for 6 hours to obtain 2.0 g of azacitidine.

Purity by HPLC: 97.57%.

EXAMPLE 10

Preparation of Azacitidine

Combined 5-azacytosine (10 g), hexamethyldisilazane (38 mL) and ammonium sulfate (0.5 g) in a round bottom flask at 25-35° C., then heated to reflux at 118-134° C. and maintained for 2 to 3 hours. The mixture was cooled to 65-70° C. and distilled under reduced pressure to give a residue, which was cooled to 25-30° C. Ethyl acetate (100 mL) was added to the residue and stirred under a nitrogen atmosphere. Added 1,2,3,5-tetra-O-acetyl-beta-D-ribofuranose (27 g) and cooled to 0-10° C. TMS-triflate (19.5 mL) was slowly added over 10-20 minutes and the mixture was allowed to warm to about 20-30° C., followed by stirring for 1 hour. The mixture was distilled under vacuum below 45° C. to obtain a residue, which was allowed to cool to 30° C. Ethyl acetate (150 mL) and anhydrous sodium carbonate (32.5 g) were added to the residue and stirred for 20-30 minutes. Filtered the reaction mixture, washed the solid with ethyl acetate (15 mL) and the filtrate was distilled under reduced pressure below 45° C. to give 30.4 g of 2,3,5-tri-O-acetyl-5-azacytidine.

Combined methanol (150 mL) and 2,3,5-tri-O-acetyl-5-azacytidine (30 g) obtained above in a round bottom flask and stirred at 25-30° C. Charged 25% NaOMe solution in methanol (2 mL) to the mixture and stirred at 25-30° C. for 60-90 minutes. The mixture was filtered and washed with methanol (20 mL). The solid was dried at 58-60° C. for 5 hours to obtain 7.7 g of azacitidine.

EXAMPLE 11

Preparation of Azacitidine

Combined methanol (200 mL) and 2,3,5-tri-O-acetyl-5-azacytidine (19 g) in a round bottom flask at 28° C. and stirred. Added diethylamine (1.04 g), heated the mixture to a temperature of 50-55° C. and maintained the mixture at this temperature until completion of the reaction. Cooled the mixture to 30° C., then filtered and washed the solid with methanol (20 mL). The solid was dried at 75° C. for 4 hours to obtain 1.3 g of azacitidine.

EXAMPLE 12

Preparation of Azacitidine

Combined hexamethyldisilazane (35 mL) and 5-azacytosine (10 g) in a round bottom flask at 28° C. Added ammonium sulfate (0.5 g), heated to about 110-130° C., and maintained for 3 hours to obtain a homogenous mixture. The mixture was distilled under vacuum at 80° C. to give a residue. Added ethyl acetate (100 mL) to the residue and stirred under a nitrogen atmosphere for dissolution. Added 1,2,3,5-tetra-O-acetyl-beta-D-ribofuranose (27.2 g) to the mass and cooled to 0-10° C. Triflic acid (9.4 ml) was slowly added over 10-30 minutes and the mixture was allowed to attain a temperature of 40-45° C., which was maintained for 1 hour. The mixture was distilled under vacuum below 45° C. to give a residue. Added dichloromethane (100 ml) to the residue and stirred for dissolution. Cooled the mixture to 20-30° C., charged water (100 mL) and stirred for 10-20 minutes. Separated the organic layer, dried with sodium sulphate, distilled under vacuum below 45° C., and further co-distilled with ethyl acetate (20 mL) to obtain a residue. Added ethyl acetate (150 mL) and anhydrous sodium carbonate (10 g) to the residue, and stirred for 20-30 minutes. Filtered the mixture through a Hyflow bed and washed with ethyl acetate (20 mL). The filtrate was distilled under reduced pressure below 45° C. to give 20.8 g of 2,3,5-tri-O-acetyl-5-azacytidine.

Combined methanol (200 mL) and 2,3,5-tri-O-acetyl-5-azacytidine (20.8 g) obtained above in a round bottom flask at 28° C. and stirred. Charged 25% NaOMe solution in methanol (1.0 mL) to the mixture and stirred at 28° C. for 1 hour. Filtered the mixture and washed the solid with methanol (10 mL). The solid was dried at 80-85° C. to obtain 4.1 g of azacitidine.

Purity by HPLC: 99.06%.

Combined azacitidine (3 g, Purity: 99.06%) and dimethylsulfoxide (21 mL, pre-heated to about 88-90° C.) and stirred for 30 minutes. Methanol (45 mL) was added to the solution at the same temperature over 30 minutes and stirred for 10 minutes. The suspension was allowed to cool to about 25-30° C. and stirred for 30 minutes. The solid was filtered, washed with methanol (15 mL) and dried for 2 hours at about 75° C. to obtain 2.1 g of azacitidine.

Purity by HPLC: 99.97%.

EXAMPLE 13

Preparation of Azacitidine Form I

Combined hexamethyldisilazane (568.8 mL), 5-azacytosine (200 g) and acetonitrile (600 mL) in a round bottom flask at 28° C., and added ammonium sulfate (10 g). The mixture was heated to about 79° C. and maintained for 3 hours to obtain a homogenous mixture. The mixture was distilled under vacuum to give a concentrated mass. Added ethyl acetate (400 mL) to the concentrated mass and stirred under a nitrogen atmosphere for dissolution. Distilled the mass under vacuum to remove ethyl acetate. Added ethyl acetate (400 mL) to the mass and distilled under vacuum to remove ethyl acetate. Added ethyl acetate (2000 mL) and 1,2,3,5-tetra-O-acetyl-beta-D-ribofuranose (539.5 g), cooled to 0-10° C. and stirred under a nitrogen atmosphere. Triflic acid (189.5 ml) was slowly added over 30-45 minutes and the mixture was heated to 44-48° C., then maintained for 1 hour. The mixture was distilled under vacuum below 46° C. to give a residue. Added dichloromethane (2000 mL) to the residue and stirred for dissolution. Cooled the mixture to 20-30° C., charged 2% HCl solution (2000 mL) and stirred for about 50 minutes. Added 10% sodium carbonate solution (3000 mL) slowly. Separated the organic layer and distilled under vacuum below 45° C., then further co-distilled with methanol (2×400 mL) to obtain 2,3,5-tri-O-acetyl-5-azacytidine.

Combined methanol (7000 mL) and 2,3,5-tri-O-acetyl-5-azacytidine obtained above in a round bottom flask at 28° C., and added n-butylamine (80 mL). The mass was heated to about 57-61° C. and maintained for about 1 hour. Filtered the mixture and washed the solid with methanol (800 mL). The solid was dried at about 55° C. to obtain 186 g of azacitidine.

Purity by HPLC: 98.10%; Impurity A: 0.1%; Impurity B: not detected; Impurity C: not detected; Impurity D: not detected; Impurity E: 1.48%.

ROI: 0.08%.

Particle size distribution: $D_{10}$: 10.799 μm; $D_{50}$: 43.965 μm; $D_{90}$: 111.464 μm; mean particle size: 54.681 μm.

Combined azacitidine (180 g) and dimethylsulfoxide (1440 mL) in a round-bottom flask at about 28° C. and stirred for dissolution. Added toluene (2700 mL) and stirred at 25-30° C. for about 3 hours. The solid was filtered, washed with toluene (540 mL), and suction dried.

Combined the wet solid with dimethylsulfoxide (882 mL) in a round-bottom flask at about 28° C. and stirred for dissolution. Added toluene (1890 mL) and stirred at 25-30° C. for about 3 hours. The solid was filtered, washed with toluene (380 mL), and suction dried. The solid was dried at about 55° C. under vacuum to give 101 g of the title compound.

Purity by HPLC: 99.84%; Impurity A: not detected; Impurity B: 0.04%; Impurity C: not detected; Impurity D: not detected; Impurity E: 0.01%.

ROI: 0.05% w/w.

XRPD diffraction pattern substantially in accordance with FIG. 1.

Particle size distribution: $D_{10}$: 34.291 μm; $D_{50}$: 118.359 μm; $D_{90}$: 284.63 μm; mean particle size: 141.771 μm.

EXAMPLE 14

Preparation of Azacitidine Form I

Combined azacitidine (40 g) and dimethylsulfoxide (200 mL) in a round-bottom flask at about 28° C. and stirred for dissolution. Added carbon (6 g) and stirred for about 30 minutes, then filtered the mass through a Hyflow bed and washed the bed with dimethylsulfoxide (120 mL). The filtrate was placed into a round bottom flask and toluene (600 mL) was added. The mass was stirred at 25-30° C. for about 4 hours, 30 minutes and the solid was filtered, washed with toluene (120 mL) and suction dried to give a wet compound (42.5 g). The wet compound obtained was divided into two parts.

Part I:
The wet compound (21.0 g) was dried at about 50° C. under vacuum to give 14.7 g of the title compound.
Purity: 99.89%; Impurity A: 0.02%; Impurity B: 0.01%; Impurity C: not detected; Impurity D: not detected; Impurity E: not detected.
XRPD diffraction pattern substantially in accordance with FIG. 1.

Figure 3:
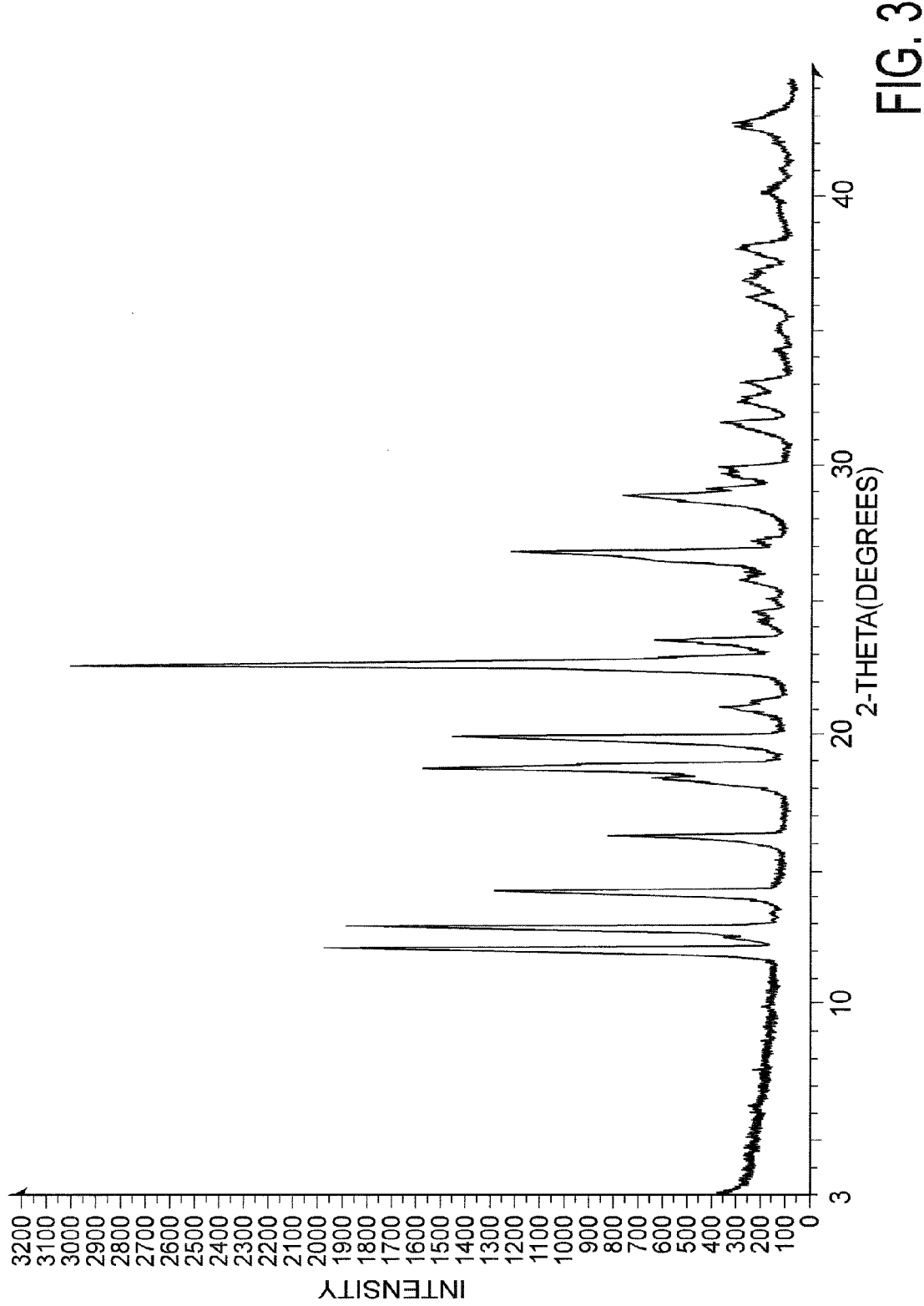
FIG. 3 is an example of an X-ray powder diffraction pattern of azacitidine crystalline Form I, obtained according to Example 13.
Figure 4:
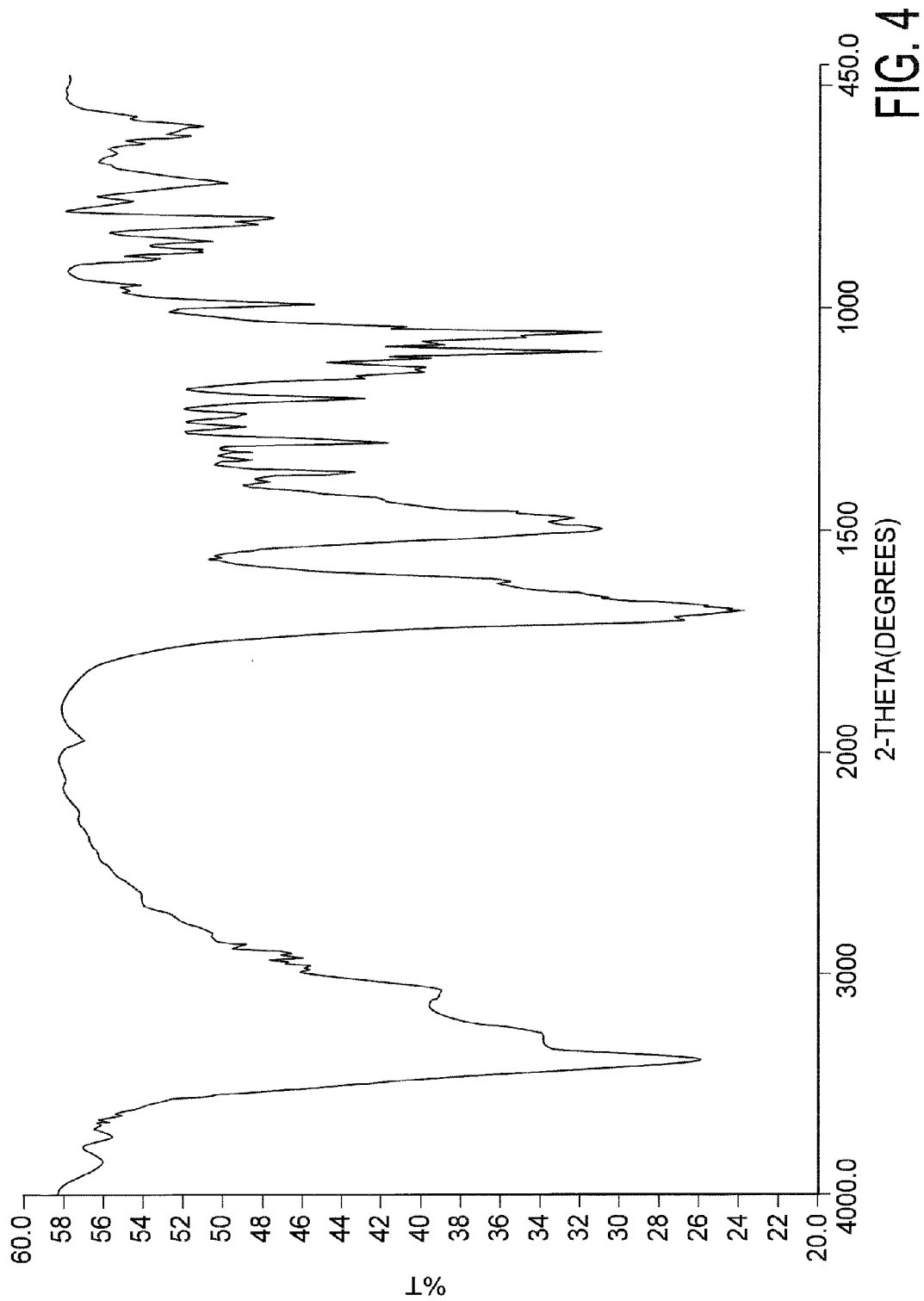
FIG. 4 is an example of an infrared (IR) absorption spectrum of azacitidine crystalline Form I, obtained according to Example 13.

Part II:
The wet compound (21.5 g) was combined with dimethylsulfoxide (98 mL) in a round-bottom flask at about 28° C. and stirred for dissolution. Added toluene (210 mL) and the mixture was stirred at 25-30° C. for about 3 hours. The solid was filtered, washed with toluene (42 ml), and suction dried. The wet solid was dried at about 50° C. under vacuum to give 12.6 g of the title compound.
Purity: 99.98%; Impurity A: not detected; Impurity B: not detected; Impurity C: not detected; Impurity D: not detected; Impurity E: 0.01%.
ROI: 0.05% w/w.
XRPD diffraction pattern substantially in accordance with FIG. 3.
IR spectrum substantially in accordance with FIG. 4.

The invention claimed is:

1. A process for preparing azacitidine, comprising:
a) silylating 5-azacytosine to give a compound of Formula II,

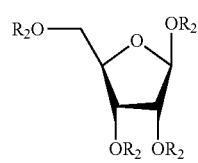

wherein $R_1$ is an optionally substituted $C_1$-$C_5$ alkyl group;
b) coupling a compound of Formula II with a compound of Formula III:

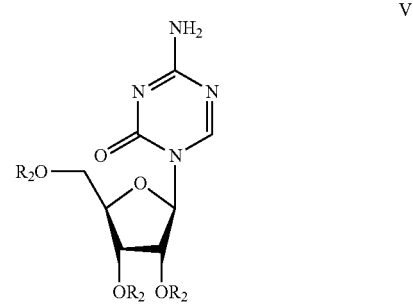

wherein $R_2$ is an optionally substituted acyl or aroyl group, in an ester solvent, in the presence of a non-Lewis Acid compound selected from trifluoromethanesulfonic acid, trichloromethanesulfonic acid, or methanesulfonic acid to provide a compound of Formula V; and

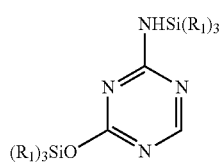

c) converting a compound of Formula V to azacitidine by hydrolytic removal of all of the acyl or aroyl groups.

2. The process of claim 1, wherein the conversion of a compound of Formula V to azacitidine in step c) is carried out in a $C_1$-$C_4$ alcohol solvent.

3. The process of claim 2, wherein a $C_1$-$C_4$ alcohol is selected from methanol, ethanol, and n-propanol.

4. The process of claim 1, wherein the conversion of a compound of Formula V to azacitidine in step c) is conducted in the presence a base or by sparging with ammonia gas.

5. The process of claim 4 wherein a base comprises an alkali metal hydroxide, metal alkoxide, alkali metal carbonate, or an organic base.

6. The process of claim 4, wherein a base comprises sodium hydroxide, potassium hydroxide, sodium methoxide, sodium carbonate, or potassium carbonate.

7. The process of claim 4, wherein a base comprises diethylamine, n-butylamine, or propylamine.

8. The process of claim 4, wherein a base comprises n-butylamine.

9. The process of claim 1, wherein step b) further comprises:
quenching a reaction mass after coupling, by adding aqueous hydrochloric acid;
(ii) adding a base to the reaction mass; and
(iii) recovering a compound of Formula V.

10. The process of claim 1, wherein the ester solvent is selected from ethyl acetate, n-propyl acetate, n-butyl acetate, or t-butyl acetate.

* * * * *